United States Patent

Lukàc et al.

Patent Number: 4,532,358
Date of Patent: Jul. 30, 1985

[54] PROCESS FOR THE MANUFACTURE OF 3-HYDROXY-2,6,6,-TRIMETHYL-2 CYCLOHEXEN-1-ONE

[75] Inventors: Teodor Lukàc, Aesch; Milan Soukup, Stein; Erich Widmer, Münchenstein, all of Switzerland

[73] Assignee: Hoffmann-La Roche Inc., Nutley, N.J.

[21] Appl. No.: 639,544

[22] Filed: Aug. 10, 1984

[30] Foreign Application Priority Data

Aug. 23, 1983 [CH] Switzerland .......................... 4593/83

[51] Int. Cl.³ .............................................. C07C 45/68
[52] U.S. Cl. ................................................... 568/341
[58] Field of Search ......................................... 568/341

[56] References Cited

U.S. PATENT DOCUMENTS 4,359,586  11/1982  Ho et al. ............................. 568/341
4,371,711  2/1983   Saito et al. .......................... 568/341

OTHER PUBLICATIONS

Suzuki et al., "J. Amer. Chem. Soc.", vol. 102, pp. 2095–2096, (1980).

*Primary Examiner*—Werren B. Lone
*Attorney, Agent, or Firm*—Jon S. Saxe; Bernard S. Leon; Frank P. Hoffman

[57] ABSTRACT

A process for the manufacture of 3-hydroxy-2,6,6,-trimethyl-2-cyclohexen-2-one, an intermediate in canthaxanthin synthesis, by isomerizing 1,1,3-trimethyl-7-oxabicyclo[4.1.0]heptan-2-one in the presence of a palladium(O) complex of an acetone derivative of the formula $$R^1-CH=\underset{R^3}{C}-\underset{O}{\overset{\|}{C}}-\underset{R^4}{C}=CH-R^2 \qquad \text{III}$$

wherein $R^1$ and $R^2$ are aryl and $R^3$ and $R^4$ are hydrogen or monovalent hydrocarbon groups optionally carrying a carbonyl function, a bis-(diphenylphosphino) derivative of the formula $$(R^5)_2P-R^6-P(R^5)_2$$

wherein $R^5$ is phenyl or tolyl and $R^6$ is a $C_2$–$C_4$-alkylene group optionally substituted with one or more inert organic groups, and a triarylphosphine of the formula $$P(R^7)_3$$

wherein $R^7$ is an optionally alkyl-substituted phenyl group.

15 Claims, No Drawings

PROCESS FOR THE MANUFACTURE OF 3-HYDROXY-2,6,6,-TRIMETHYL-2 CYCLOHEXEN-1-ONE

BACKGROUND OF THE INVENTION

1. Field of the Invention

The present invention is concerned with a novel process for the manufacture of 3-hydroxy-2,6,6-trimethyl-2-cyclohexen-1-one, a key compound in canthaxanthin syntheses, by the isomerization of an epoxide.

2. Brief Description of the Related Art

Isomerizations of epoxides to carbonyl compounds in the presence of Lewis acids have been known for a long time. Because these reactions are often technically unsatisfactory with respect to yields and/or reaction conditions, the use of noble metal catalysts has also been investigated for some time.

Isomerizations of α-β-epoxyketones to β-diketones in the presence of palladium (O) catalysts are described in Japanese Kokai No. 81/15216 and in J. Amer. Chem. Soc. 102. 2096 (1980). However, epoxyketones having an α-alkyl substituent generally react only sluggishly according to the stated process and give only low yields of β-diketone after relatively long reaction times.

DESCRIPTION OF THE INVENTION

It has now been found that 1,3,3-trimethyl-7-oxabicyclo[4.1.0]heptan-2-one can be isomerized in accordance with the process provided by the invention with considerably shorter reaction times and in clearly improved yield.

The process provided by the invention for the manufacture of 3-hydroxy-2,6,6-trimethyl-2-cyclohexen-1-one of the formula

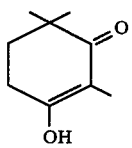

I comprises isomerizing 1,3,3-trimethyl-7-oxabicyclo[4.1.0]heptan-2-one of the formula

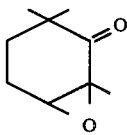

II in the presence of (a) a palladium(O) complex of an acetone derivative of the general formula

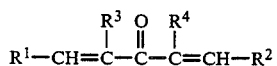

III wherein $R^1$ and $R^2$ are aryl and $R^3$ and $R^4$ are hydrogen or monovalent hydrocarbon groups optionally carrying a carbonyl function.

(b) a bis-(diphenylphosphino) derivative of the general formula $$(R^5)_2P-R^6-P(R^5)_2$$

IV wherein $R^5$ is phenyl or tolyl and $R^6$ is a $C_2$–$C_4$-alkylene group optionally substituted with one or more inert organic groups, and (c) a triarylphosphine of the general formula $$P(R^7)_3$$

V wherein $R^7$ is an optionally alkyl-substituted phenyl group.

The compound of formula I generally exists predominantly in the form given above. The tautomeric 2,4,4-trimethyl-1,3-cyclohexanedione is also occasionally given in the literature for this compound.

The substituents $R^3$ and $R^4$ in formula III above are hydrogen or monovalent hydrocarbon groups such as alkyl, alkenyl, aryl, arylalkyl, arylalkenyl etc which optionally carry a carbonyl function. A carbonyl function, when present, is preferably situated in the 1-position of the group. Especially preferred among such groups are the arylacrylyl groups. Preferably, at least one of the substituents $R^3$ and $R^4$ is hydrogen. Especially preferred ligands of formula III are therefore those in which $R^4$ is hydrogen and $R^3$ is hydrogen or arylacrylyl, especially hydrogen.

The term "aryl" signifies in the scope of the present invention (and especially in connection with the groups $R^1$–$R^4$ in formula III) aromatic carbocyclic groups such as phenyl, naphthyl and the like which can be unsubstituted or substituted with inert organic groups such as alkyl, alkenyl, hydroxy, chlorine etc. Preferred aryl groups are tolyl and especially phenyl.

Examples of preferred ligands of formula III are dibenzylidene acetone and tribenzylidene acetylacetone. Examples of preferred palladium(O) complexes are accordingly bis-(dibenzylidene acetone)palladium(O) and tris-(tribenzylidene acetylacetone)dipalladium(O)-chloroform.

The substituent $R^6$ in formula IV is a $C_2$–$C_4$-alkylene group which is optionally substituted with one or more inert organic groups such as alkyl, alkenyl, hydroxy, chlorine etc, preferably methyl. Preferred alkylene groups are those containing 2 or 3 carbon atoms, especially ethylene. Phenyl is the preferred group $R^5$. 1,2-bis-(diphenylphosphino)-ethane is therefore the especially preferred bis-(diphenylphosphino) derivative.

The substituent $R^7$ in formula V is preferably a group containing 6 to 10 carbon atoms such as phenyl, tolyl, xylyl and the like. Triphenylphosphine is the especially preferred triarylphosphine.

The isomerization in accordance with the invention of the compound of formula II can be carried out in an inert organic solvent, for example a hydrocarbon such as toluene, xylene, decalin and the like. However, the isomerization is preferably carried out in the absence of a solvent. Temperature and pressure are not critical aspects in this reaction. However, the reaction is generally carried out at a temperature of about 80°–200° C. Preferred temperature ranges are 120°–160° C. and especially 140°–150° C.

The process provided by the invention can be carried out in the presence of catalytic amounts of palladium(O) complex, bis-(diphenylphosphino) derivative and triarylphosphine. However, the amount of palladium(O) complex advantageously lies at about 1–10 mol-%, especially about 3–8 mol-%, based on the starting material of formula II. The amount of bis-(diphenylphosphino)

derivative of formula IV generally amounts to about 0.5–5 mol equivalents, preferably about 1–3 mol equivalents, based on palladium used. The amount of triarylphosphine of formula V usually lies at about 0.5–5 mol equivalents, preferably about 1–3 mol equivalents, based on palladium used. The given concentration ranges are, however, not critical and, in particular, higher amounts of palladium(O) complex and compounds of formulae IV and V can also be used.

The working-up of the reaction mixture can be carried out in a manner known per se. Preferably, the corresponding enolate of the compound of formula I is extracted from the mixture by means of alkali (e.g. sodium hydroxide solution). In this manner there is obtained directly a product of high purity with less purification requirements.

The compounds of formulae I–V and the palladium(O) complexes of the compounds of formula III are known or are analogues of known compounds and can be prepared according to methods known per se.

The further conversion of the compound of formula I into canthaxanthin can be carried out in a manner known per se, for example according to the process described in German Offenlegungsschrift No. 2625259.

The process provided by the invention is illustrated in more detail by the following Example.

EXAMPLE 1

15.4 g of 1,3,3-trimethyl-7-oxabicyclo-[4.1.0]heptan-2-one, 1.8 g of triphenylphosphine and 2.76 g of 1,2-bis-(diphenylphosphino)-ethane were placed under argon gasification in a round flask equipped with a thermometer and a reflux condenser and the mixture was treated with 2.0 g of bis-(dibenzylidene acetone)palladium(O). The reaction vessel was then immersed in an oil-bath preheated to 150° C. and the reaction mixture was stirred at this temperature with a magnetic stirrer for 1 hour under continued argon gasification. A gas-chromatographical analysis of the mixture obtained without an internal standard gave peaks for 3-hydroxy-2,6,6-trimethyl-2-cyclohexen-1-one (81.9 area %) and 2,6,6-trimethyl-2-cyclohexen-1-one (18 area %). For the working-up, the reaction mixture, cooled to room temperature, was taken up in 20 ml of ethyl acetate and filtered over silica gel in a sintered glass suction filter. The content of the suction filter was rinsed three times with 150 ml of ethyl acetate each time. The filtrate was evaporated to constant weight in a rotary evaporator under a water-jet vacuum at a bath temperature of 40° C. The residue (21.5 g of a yellowish oil) was dissolved in 100 ml of diethyl ether and the solution was added to a separating funnel S₁. Two further separating funnels S₂ and S₃ were each charged with 100 ml of diethyl ether. Then, three 150 ml portions of 3N sodium hydroxide solution were passed in succession and with good intermixing through the three extraction vessels S₁–S₃. The ether phases were discarded. The combined alkaline extracts were acidified cautiously (pH about 1) with about 300 ml of concentrated hydrochloric acid while cooling with ice and then saturated with 500 g of sodium chloride while stirring. Three separating funnels S₄–S₆ were each charged with 200 ml of ethyl acetate. Thereafter, the aqueous product solution and subsequently three 150 ml portions of saturated sodium chloride solution were passed in succession and with good intermixing through the three extraction vessels S₄–S₆. The combined organic phases were dried over sodium sulphate. The drying agent was filtered off under suction and rinsed on the suction filter twice with 100 ml of ethyl acetate each time. The filtrate was evaporated in a rotary evaporator under a water-jet vacuum at a bath temperature of 40° C. and the residue was dried in a high vacuum. There were obtained 10.1 g (65.6%) of 3-hydroxy-2,6,6-trimethyl-2-cyclohexen-1-one in the form of colourless crystals with a purity of 99.6%: m.p. 112°–114° C. after recrystallization from diisopropyl ether.

We claim:

1. A process for the manufacture of 3-hydroxy-2,6,6-trimethyl-2-cyclohexen-1-one of the formula

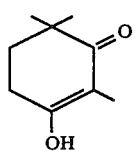

which process comprises isomerizing 1,3,3-trimethyl-7-oxabicyclo[4.1.0]heptan-2-one of the formula

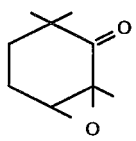

in the presence of
(a) a palladium(0) complex of an acetone derivative of the formula

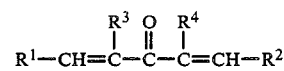

wherein $R^1$ and $R^2$ are aryl and $R^3$ and $R^4$ are hydrogen or monovalent hydrocarbon groups optionally carrying a carbonyl function, (b) a bis-(diphenylphosphino) derivative of the formula $$(R^5)_2P-R^6-P(R^5)_2 \qquad IV$$

wherein $R^5$ is phenyl or tolyl and $R^6$ is a $C_2$–$C_4$-alkylene group optionally substituted with one or more inert organic groups, and (c) a triarylphosphine of the formula $$P(R^7)_3 \qquad V$$

wherein $R^7$ is an optionally alkyl-substituted phenyl group.

2. A process according to claim 1, wherein the isomerization is carried out at a temperature of 80°–200° C.

3. A process according to claim 1, wherein the isomerization is carried out at a temperature of 120°–160° C.

4. A process according to claim 1, wherein the isomerization is carried out in the presence of palladium(O) complex of an acetone derivative of formula III in which $R^3$ and $R^4$ are hydrogen.

5. A process according to claim 1, wherein the isomerization is carried out in the presence of a palladium(O) complex of an acetone derivative of formula III in which $R^1$ and $R^2$ are phenyl or tolyl.

6. A process according to claim 1, wherein the isomerization is carried out in the presence of a palladium(O) complex of an acetone derivative of formula III in which $R^1$ and $R^2$ are phenyl.

7. A process according to claim 1, wherein the isomerization is carried out in the presence of bis-(dibenzylidene acetone) palladium(O).

8. A process according to claim 1, wherein the isomerization is carried out in the presence of a bis-(diphenylphosphino) derivative of formula IV in which $R^6$ is ethylene.

9. A process according to claim 1, wherein the isomerization is carried out in the presence of a bis-(diphenylphosphino) derivative of formula IV in which $R^5$ is phenyl.

10. A process according to claim 1, wherein the isomerization is carried out in the presence of a triarylphosphine of formula V in which $R^7$ is phenyl or tolyl.

11. A process according to claim 1, wherein the isomerization is carried out in the presence of a triarylphosphine of formula V in which $R^7$ is phenyl.

12. A process according to claim 1, wherein the reaction is carried out in the presence of 1-10 mol-%, of palladium(O) complex based on the starting material of formula II.

13. A process according to claim 1, wherein the reaction is carried out in the presence of 3-8 mol-%, of palladium(O) complex based on the starting material of formula II.

14. A process according to claim 1, wherein the reaction is carried out in the presence of, in each case, 0.5-5 mol equivalents of bis-(diphenylphosphino) derivative of formula IV and of triarylphosphine of formula V based on palladium used.

15. A process according to claim 1, wherein the reaction is carried out in the presence of, in each case, 1-3 mol equivalents of bis-(diphenylphosphino) derivative of formula IV and of triarylphosphine of formula V based on palladium used.

* * * * *